(12) United States Patent
Rangabhatla Gunneswara Subramanya et al.

(10) Patent No.: US 10,702,578 B2
(45) Date of Patent: Jul. 7, 2020

(54) OPHTHALMIC COMPOSITIONS OF CYCLOSPORINE

(71) Applicant: SHILPA MEDICARE LIMITED, Raichur (IN)

(72) Inventors: Vara Prasad Rangabhatla Gunneswara Subramanya, Bangalore (IN); Sandeep Kalepu, Bangalore (IN); Ratna Phani Ayalasomayajula, Bangalore (IN)

(73) Assignee: SHILPA MEDICARE LIMITED, Raichur, Karnataka ( * ) Notice: Subject to any disclaimer, the term of this patent is extended or adjusted under 35 U.S.C. 154(b) by 0 days.

(21) Appl. No.: 16/492,171

(22) PCT Filed: Aug. 1, 2018

(86) PCT No.: PCT/IB2018/055757
§ 371 (c)(1),
(2) Date: Sep. 9, 2019

(87) PCT Pub. No.: WO2019/025986
PCT Pub. Date: Feb. 7, 2019

(65) Prior Publication Data
US 2020/0147170 A1 May 14, 2020

(30) Foreign Application Priority Data
Aug. 2, 2017 (IN) .............................. 201741027472

(51) Int. Cl.
| | | |
|---|---|---|
| *A61K 38/00* | (2006.01) |
| *A61K 38/13* | (2006.01) |
| *A61P 27/02* | (2006.01) |
| *A61K 9/00* | (2006.01) |
| *A61K 31/715* | (2006.01) |
| *A61K 47/26* | (2006.01) |
| *A61K 47/44* | (2017.01) |

(52) U.S. Cl.
CPC ............ *A61K 38/13* (2013.01); *A61K 9/0048* (2013.01); *A61K 31/715* (2013.01); *A61K 47/26* (2013.01); *A61K 47/44* (2013.01); *A61P 27/02* (2018.01)

(58) Field of Classification Search
CPC combination set(s) only.
See application file for complete search history.

(56) References Cited

U.S. PATENT DOCUMENTS

| 8,455,462 B2 * | 6/2013 | Del Prete | ............. A61K 31/715 |
| | | | 514/54 |
| 2005/0014691 A1 * | 1/2005 | Bakhit | .................. A61K 38/17 |
| | | | 514/12 |
| 2009/0286718 A1 * | 11/2009 | Stringer | ................. A61K 38/13 |
| | | | 514/11 |

FOREIGN PATENT DOCUMENTS

| EP | 2845602 A1 | 3/2015 |
| WO | 2016060532 A1 | 4/2016 |

* cited by examiner

*Primary Examiner* — James H Alstrum-Acevedo
*Assistant Examiner* — Mercy H Sabila

(57) ABSTRACT

The present invention relates to the ophthalmic composition comprising from about 0.03% to about 2% by weight of cyclosporine, from about 0.05% to about 5% by weight of tamarind seed polysaccharide and a pharmaceutically acceptable carrier. Further the invention relates to the process for preparation of ophthalmic compositions and its use for the treatment of dry eye.

5 Claims, 8 Drawing Sheets

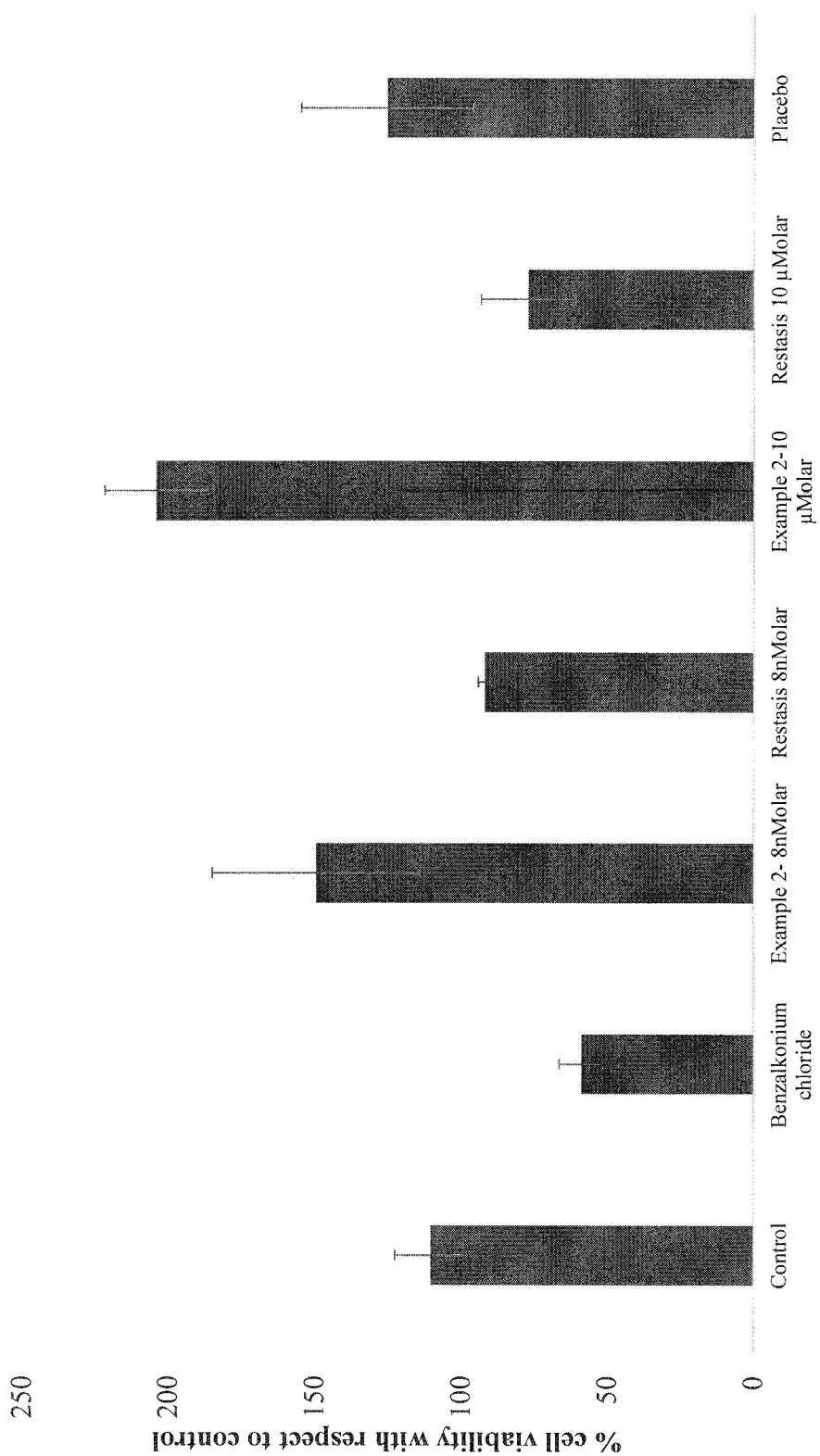
Figure 1: 4 hours contact toxicity on rabbit corneal epithelial cells.

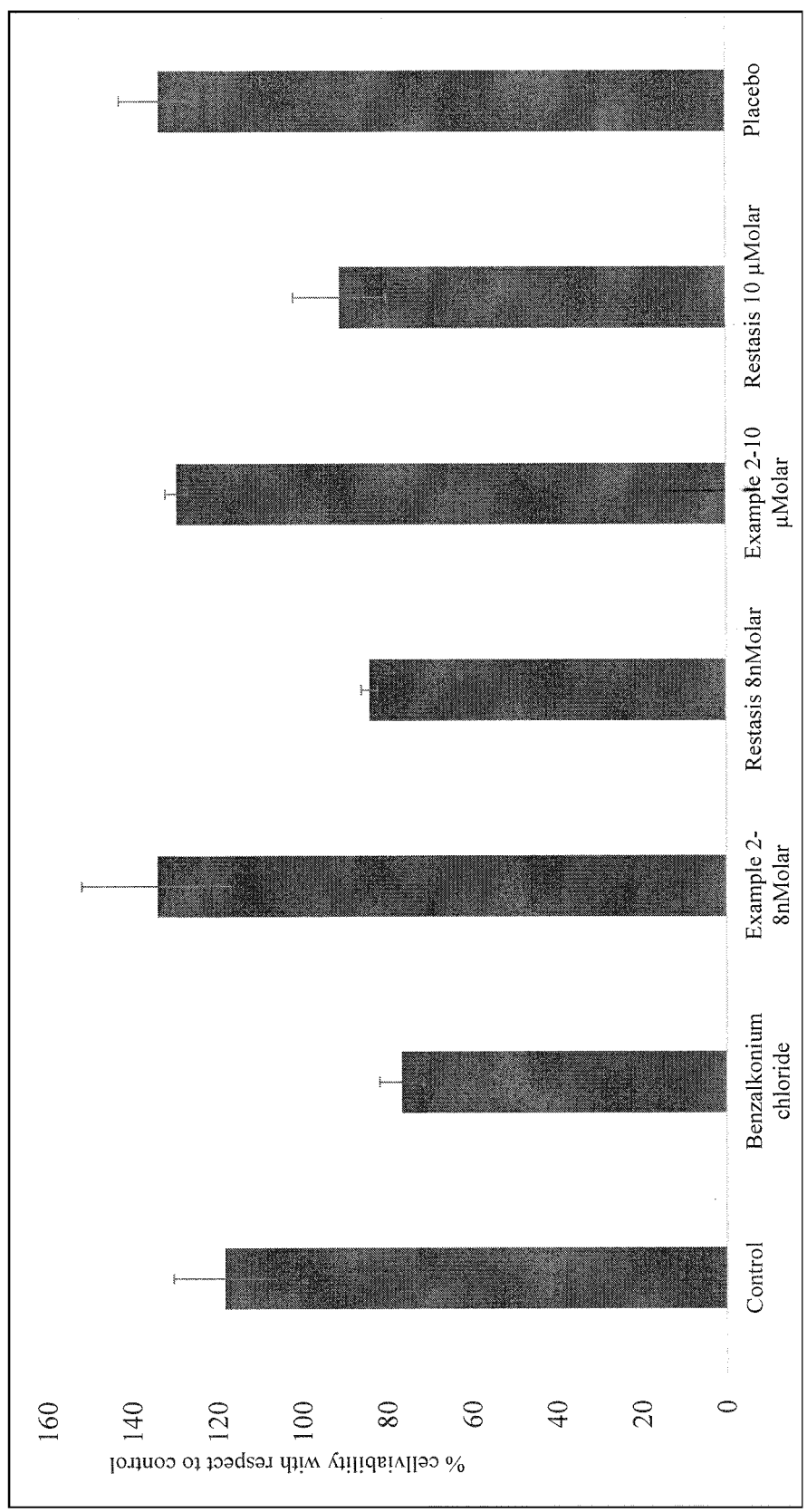
Figure 2: 24hours contact toxicity on rabbit corneal epithelial cells.

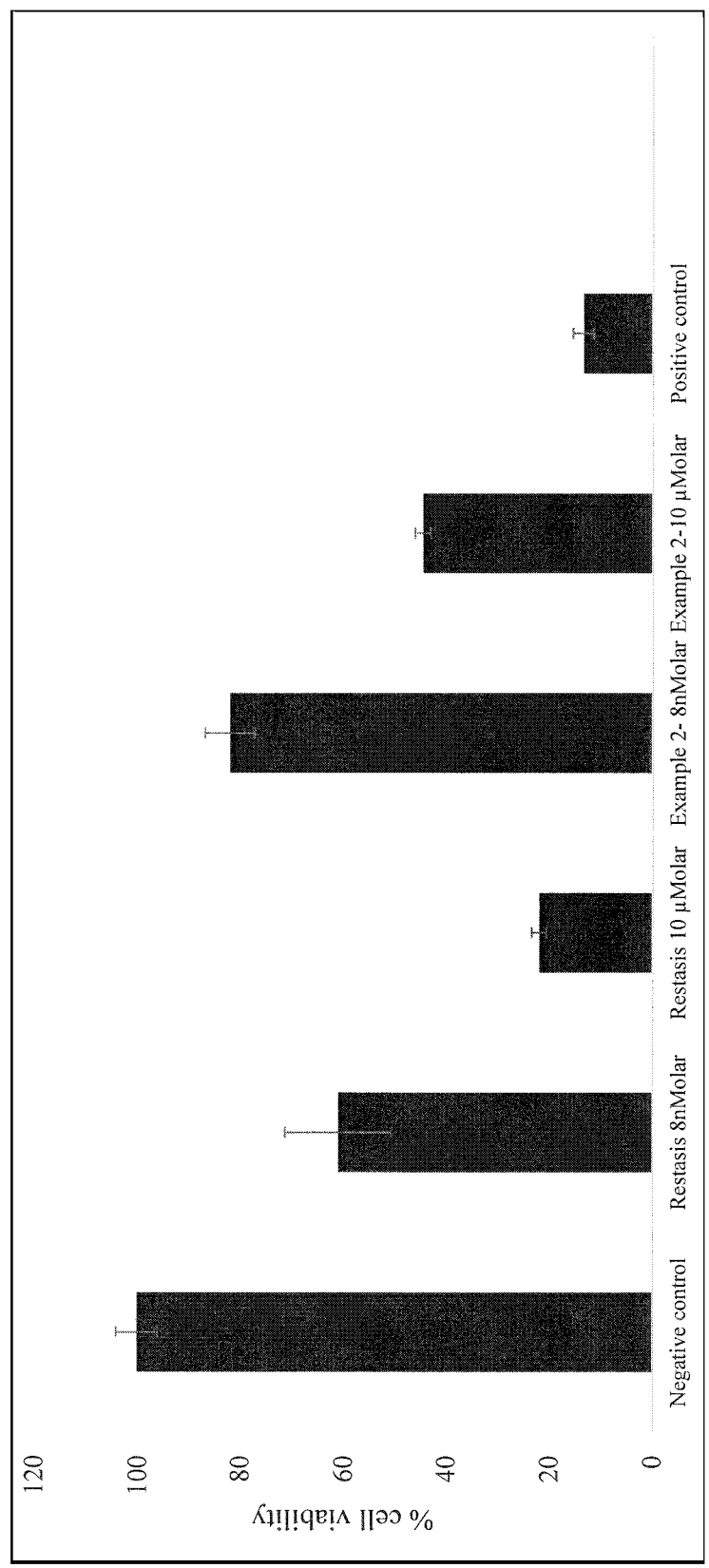
Figure 3: Short term desiccation of rabbit corneal epithelial cells and cell viability after recovery using different formulations

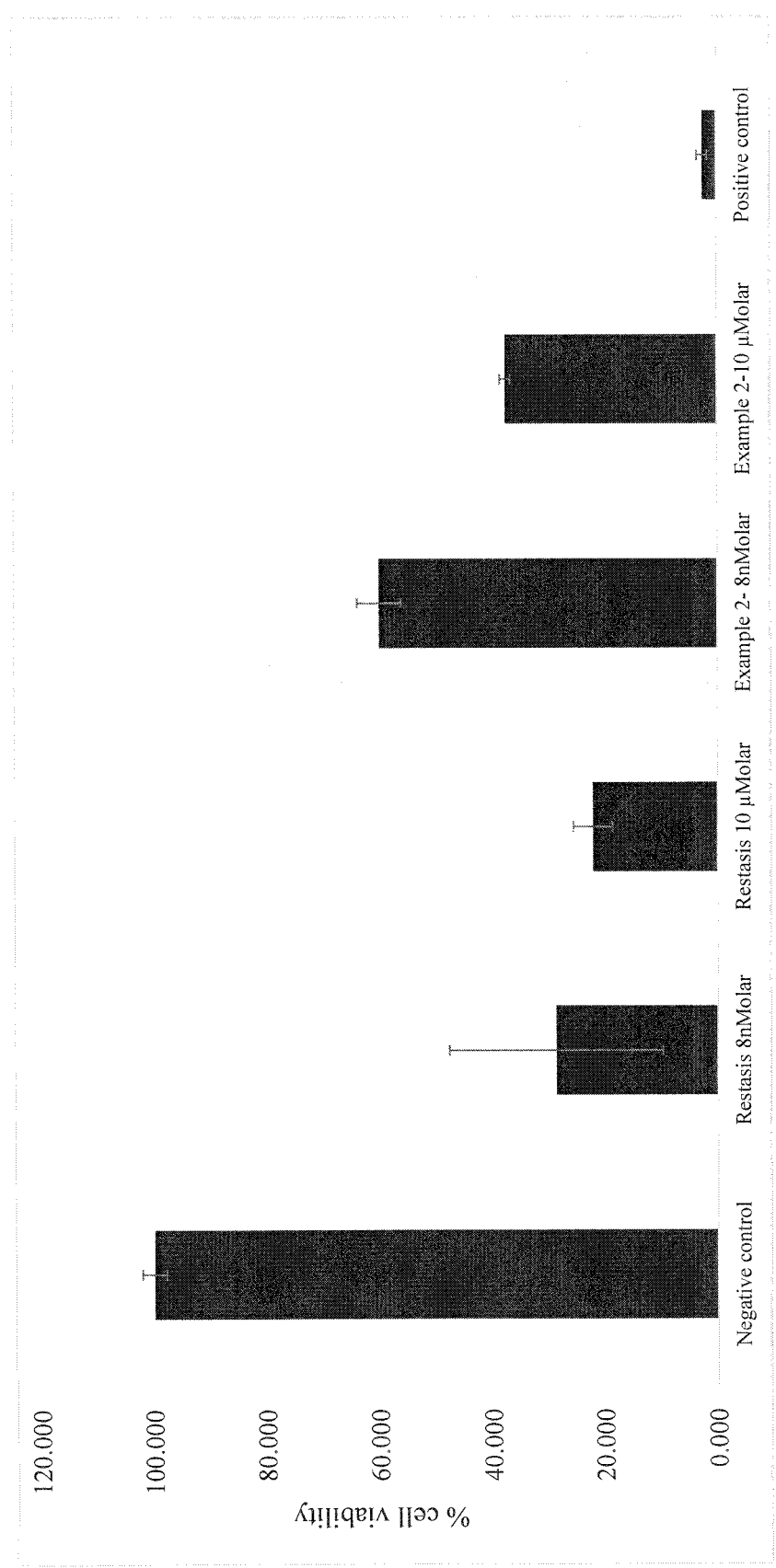
Figure 4: UV treatment of rabbit corneal epithelial cells and cell viability after recovery using different formulations

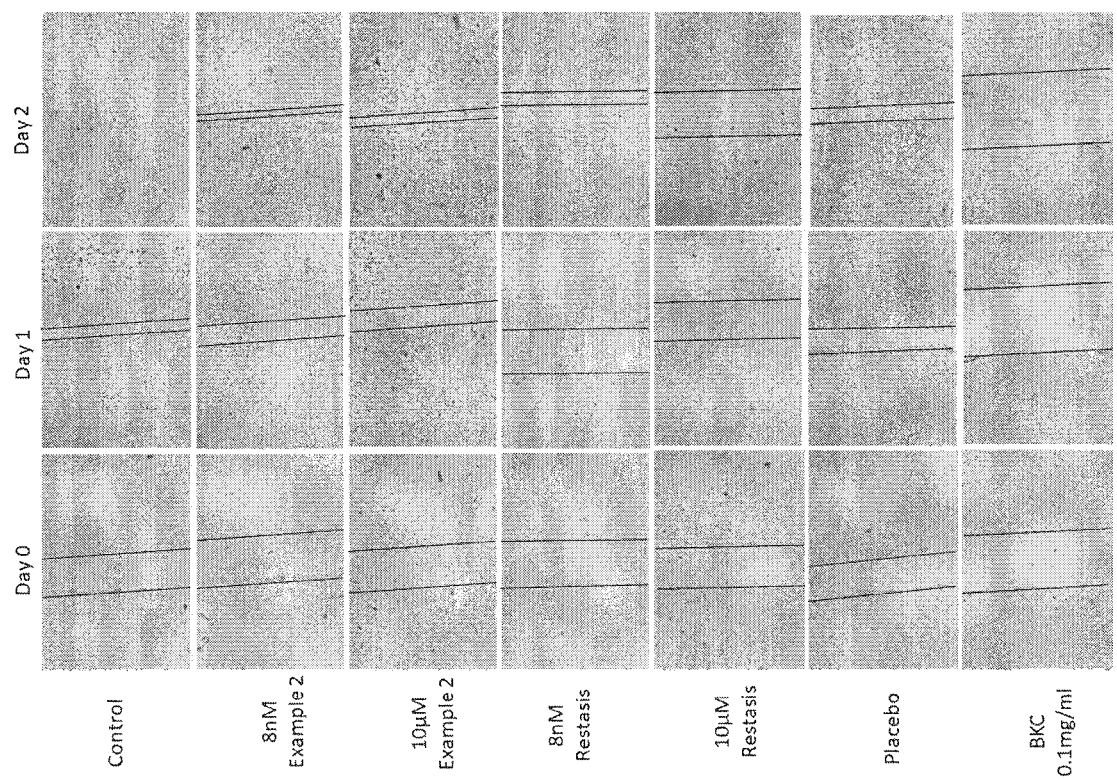
Figure 5 Corneal regeneration images

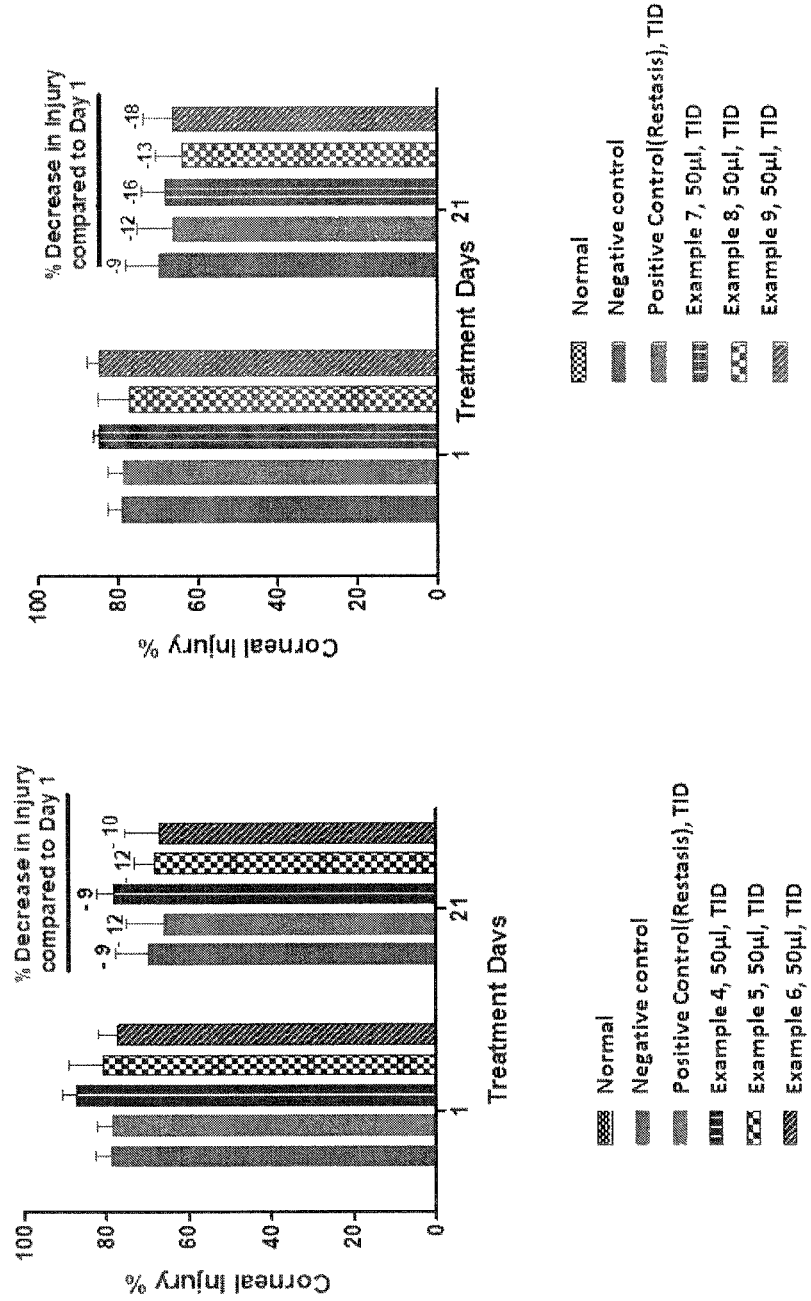
Figure 6: Percentage reduction of corneal injury with respective to control and groups 1 and 2

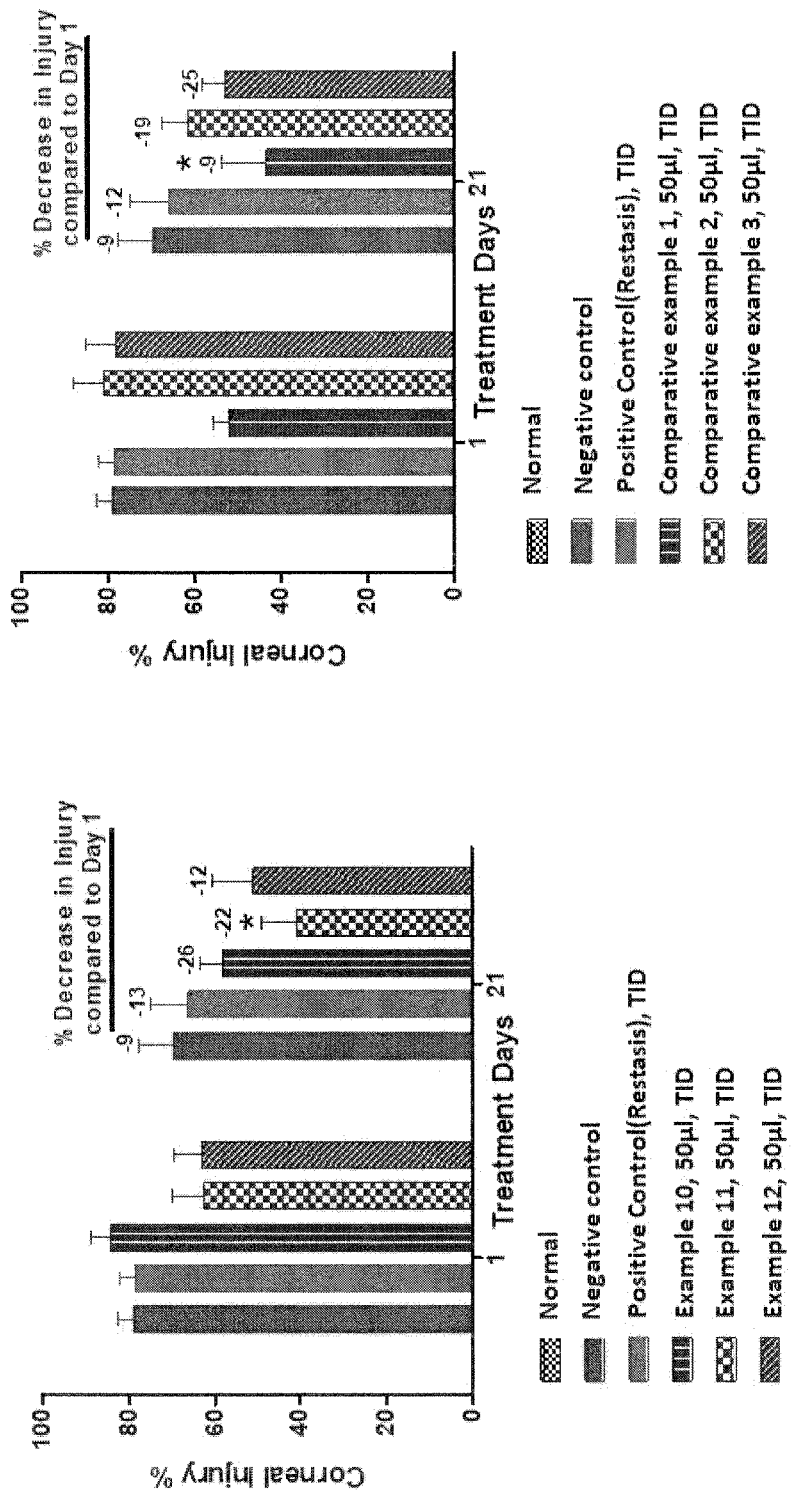
Figure 7: Percentage reduction of corneal injury with respective to control and groups 3 and Placebo

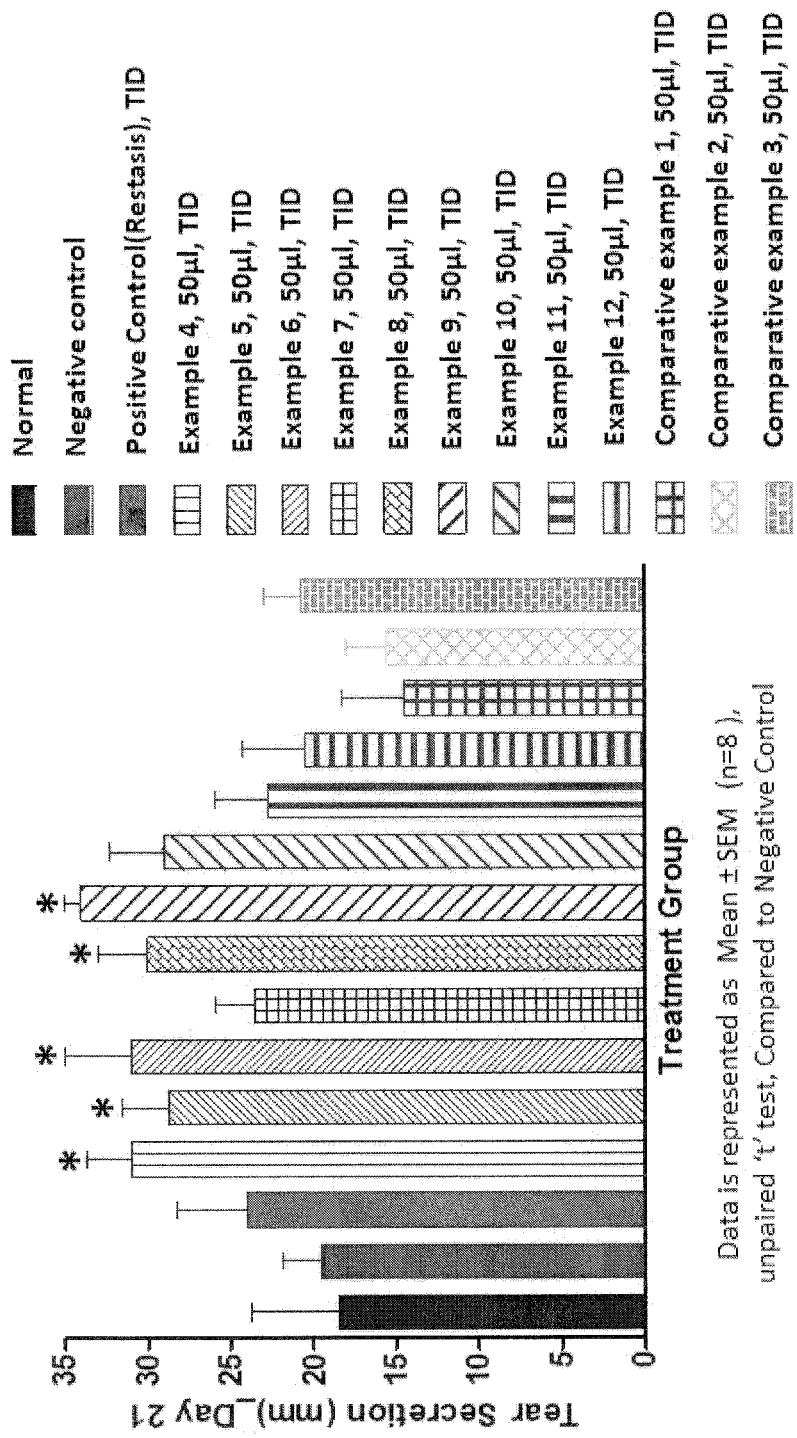
Figure 8: Percentage increase in tear production with respective to control and groups

OPHTHALMIC COMPOSITIONS OF CYCLOSPORINE

FIELD OF INVENTION

The present invention relates to ophthalmic compositions of cyclosporine and the process for preparation thereof. In embodiments of the invention, the ophthalmic composition is an aqueous ophthalmic solution comprising cyclosporine and tamarind seed polysaccharide (TSP; *Tamarindus indica* Seed Polysaccharide).

BACKGROUND OF THE INVENTION

Dry eye disease is a general term for a variety of conditions characterized by abnormalities in the tear film, where nearly half (48%) of Americans age 18 and older regularly experience dry eye symptoms. Dry eye is characterized by symptoms such as feeling that grit or some other object or material is in the eye, burning sensation, sore eyes, itchy eyes, aching sensations, heavy eyes, fatigued eyes, dryness sensation, red eyes, photophobia and blurred vision. Further the term "dry eye" syndrome is commonly used to refer to the ophthalmic condition resulting from the reduction or the instability of the tear film while, more properly, the typical alterations of the corneal surface occurring in this connection are referred to by the term "keratoconjunctivitis sicca".

The tear film consists of an inner mucous layer, a middle aqueous layer which forms the bulk of the tear film, and an outer lipid layer. The aqueous layer is secreted by the lacrimal glands and the accessory lacrimal glands, and the tear fluid is drained by the efferent tear ducts. While the underlying causes of dry eye diseases are largely unknown, it is generally accepted that they are associated with abnormalities in the meibomian glands (which secrete the lipid layer), and abnormalities in drainage through the efferent tear duct passage, changes in mucin composition and mucous viscosity may also affect tear flow.

Until recently, the methods used for the treatment of dry eye disease were topical administration of over-the-counter compositions that serve as artificial tears (such as Refresh® marketed by Allergan), ophthalmic product containing cyclosporine A (Restasis® marketed by Allergan), ophthalmic product containing lifitegrast (Xiidra® marketed by shire), or surgery to close efferent drainage.

Therefore, there is a scope in developing new formulations in this area which are less toxic and more biocompatible with more emphasis on biomimetic approach in treatment of dry eye disease.

SUMMARY OF THE INVENTION

The present invention provides an ophthalmic compositions of cyclosporine, preferably aqueous ophthalmic solutions.

One embodiment of the present invention provides an ophthalmic composition comprising cyclosporine, tamarind seed polysaccharide and a pharmaceutically acceptable carrier.

In embodiments, the present invention provides an ophthalmic composition comprising cyclosporine, tamarind seed polysaccharide and a pharmaceutically acceptable is used for the treatment of dry eye and has corneal regeneration properties.

In embodiments of the invention, the ophthalmic compositions comprising cyclosporine, tamarind seed polysaccharide and a pharmaceutically acceptable carrier do not produce the side effects such as blurred vision, increase lacrimation, eye discharge, reduced visual activity and dysgeusia, as reported in other commercially available cyclosporine ophthalmic compositions, thus providing a better safety profile.

The ophthalmic compositions of the instant disclosure are based, at least in part, on the surprising and unexpected findings that ophthalmic composition comprising from about 0.03% to about 0.07% by weight of cyclosporine, from about 0.2% to about 0.8% by weight of tamarind seed polysaccharide and pharmaceutically acceptable carrier have higher effectiveness for treatment of dry eye and has corneal regeneration.

In a further embodiment of the present invention provides an ophthalmic composition comprising cyclosporine, tamarind seed polysaccharide, hydroxypropyl methylcellulose, polysorbate 80, polyoxyl 40 hydrogenated castor oil, ethanol, sodium chloride and water for injection.

In certain aspects and embodiments, the ophthalmic composition of the present invention comprises from about 0.03% to about 2% by weight of cyclosporine, from about 0.05% to about 5% by weight of tamarind seed polysaccharide, from about 0.05% to about 2% by weight of polysorbate 80, and from about 0.3% to about 2% by weight of polyoxyl 40 hydrogenated castor oil.

In certain aspects and embodiments, the ophthalmic composition of the present invention comprises of about 0.07% by weight of cyclosporine, of about 0.8% by weight of tamarind seed polysaccharide, about 0.9% by weight of polysorbate 80 and about 0.5% by weight of polyoxyl 40 hydrogenated castor oil.

In certain aspects and embodiments, the ophthalmic composition of the present invention comprises from about 0.03% to about 2% by weight of cyclosporine, from about 0.05% to about 5% by weight of tamarind seed polysaccharide, from about 0.05% to about 2% by weight of polysorbate 80, from about 0.3% to about 2% by weight of polyoxyl 40 hydrogenated castor oil, from about 0.05% to about 5% by weight of hydroxypropyl methylcellulose, from about 0.1% to about 5% by weight of ethanol, and optionally further comprising sodium phosphate monobasic, sodium phosphate dibasic, sodium chloride, sodium hydroxide/hydrochloride and water for injection.

In certain aspects and embodiments, the ophthalmic composition of the present invention comprises of about 0.07% by weight of cyclosporine, of about 0.8% by weight of tamarind seed polysaccharide, of about 0.9% of polysorbate 80, of about 0.5% of polyoxyl 40 hydrogenated castor oil, of about 0.5% by weight of hydroxypropyl methylcellulose, of about 0.5% by weight of ethanol, and optionally further comprising sodium phosphate monobasic, sodium phosphate dibasic, sodium chloride, sodium hydroxide/hydrochloride and water for injection.

In certain aspects and embodiments, the ophthalmic composition of the present invention consists essentially of about 0.07% by weight of cyclosporine, of about 0.8% by weight of tamarind seed polysaccharide. Further the said composition comprises of about 0.9% of polysorbate 80, of about 0.5% of polyoxyl 40 hydrogenated castor oil, of about 0.5% by weight of hydroxypropyl methylcellulose, of about 0.5% by weight of ethanol and optionally further comprising sodium phosphate monobasic, sodium phosphate dibasic, sodium chloride, sodium hydroxide/hydrochloride and water for injection.

In certain aspects and embodiments, the present ophthalmic compositions demonstrate a significant improvement as compared to vehicle in tear production.

BRIEF DESCRIPTION OF DRAWINGS

FIG. 1: shows the 4 hours contact toxicity in rabbit corneal epithelial cells of control (culture media with 10% fetal bovine serum), Benzalkonium chloride (0.1%), Example-2 (8 nM & 10 µM), Restasis (8 nm & 10 µM) and Placebo (Example 2 without cyclosporine).

FIG. 2: shows 24-hour contact toxicity in rabbit corneal epithelial cells, control (culture media with 10% fetal bovine serum), Benzalkonium chloride (0.1%), Example-2 (8 nM & 10 µM), Restasis (8 nm & 10 µM) and Placebo (Example 2 without cyclosporine).

FIG. 3: shows short term desiccation of rabbit corneal epithelial cells (dry eye induction & treatment) of negative control (culture media with 10% fetal bovine serum), Restasis (8 nm & 10 µM), Example 2 (8 nm & 10 µM) and positive control (no culture media)

FIG. 4: shows UV treatment of rabbit corneal epithelial cells (radiation induced dry eye & treatment) of negative control (culture media with 10% fetal bovine serum), Restasis (8 nm & 10 µM), Example 2 (8 nm & 10 µM) and positive control (no culture media)

FIG. 5: Corneal regeneration images of BKC, Placebo (Example 2 without cyclosporine), Restasis (8 nM & 10 µM), Example 2 (8 nM & 10 µM) & Control (culture medium with 10% fetal bovine serum)

FIG. 6: Percentage reduction of alkali induced corneal damage (corneal regeneration) of Normal (untreated eye), Negative control (alkali induced corneal damaged eye), Positive control (Restasis), Example 4, 5, 6, 7, 8 & 9.

FIG. 7: Percentage reduction of alkali induced corneal damage (corneal regeneration) of Normal (untreated eye), Negative control (alkali induced corneal damaged eye), Positive control (Restasis), Example 10, 11, 12, comparative example 1, 2 & 3.

FIG. 8: Percentage enhancement of tear production (treatment of dry eye) in atropine induced eye of Normal (untreated eye), Negative control (alkali induced corneal damaged eye), Positive control (Restasis), Example 4, 5, 6, 7, 8, 9, 10, 11 & 12 and comparative example 1, 2 & 3.

DETAILED DESCRIPTION OF THE INVENTION

The present invention provides an ophthalmic compositions of cyclosporine, preferably aqueous ophthalmic solutions.

As used herein in connection with numerical values, the terms "about" mean+/−10% of the indicated value, including the indicated value.

In embodiments of the invention, ophthalmic composition comprises cyclosporine as the active ingredient from about 0.03% to about 2% by weight, preferably from about 0.03% to about 0.07%, more preferably 0.03%, 0.035%, 0.04%, 0.045%, 0.05%, 0.055%, 0.06%, 0.065%, 0.07% and 0.075% and most preferably 0.07% by weight.

In another embodiment of the present invention provides an ophthalmic composition comprising cyclosporine, tamarind seed polysaccharide (TSP) and a pharmaceutically acceptable carrier.

Tamarind seed polysaccharide is a natural polysaccharide polymer obtained from seeds of the tamarind tree, the *Tamarindus indica,* an evergreen plant that may reach 15 m of height and that produces legume fruit and that is wide spread in India, and primarily cultivated for food production. The fruit contains big seeds having a high percentage of polysaccharides, which have the function to accumulate and preserve vital energetic substances.

The term "tamarind seed polysaccharide" (*Tamarindus indica* Seed Polysaccharide or TSP, sometimes generically referred to with the term "xyloglucan") as used in the present application means any polysaccharide enriched fraction obtainable from tamarind gum (i.e tamarind kernel powder), which is commercially available in the market.

In embodiments of the invention, ophthalmic composition comprises tamarind seed polysaccharide from about 0.05% to about 5% by weight, preferably from about 0.2% to about 0.8%, more preferably 0.2%, 0.3%, 0.4%, 0.5%, 0.6%, 0.7%, 0.8%, and 0.85% and most preferably 0.8% by weight.

In embodiments of the invention, the ophthalmic composition according to the invention contains, an aqueous solution comprising from about 0.03% to about 2% by weight of cyclosporine, from about 0.05% to about 5% by weight of tamarind seed polysaccharide.

Preferably the weight concentrations in the ophthalmic composition according to the invention are comprised from about 0.03% to about 0.07% by weight of cyclosporine and from about 0.2% to about 0.8% by weight of tamarind seed polysaccharide. An embodiment which has been specifically studied in the experimental work provided below, and which has superior clinical performances regarding the treatment of dry eye and corneal regeneration for restoring the normality of the conjunctival epithelium contains in an ophthalmic solution having 0.07% by weight of cyclosporine and 0.8% by weight of tamarind seed polysaccharide.

Preferably the tamarind seed polysaccharide used in the preparation of the present invention has a molecular weight comprised in the range from 450,000 Da to 750,000 Da.

In embodiments, the present invention provides an ophthalmic composition comprising cyclosporine, tamarind seed polysaccharide and a pharmaceutically acceptable is used for the treatment of dry eye and has corneal regeneration properties.

In embodiments, the ophthalmic composition of the present invention further comprise pharmaceutically acceptable carriers. The pharmaceutically acceptable carriers are selected from surfactants, cellulose polymers, solvents and tonicity adjusting agents, buffers, pH adjusting agents and preservatives.

As used herein, the term "micelle" refers to an aggregate of surfactant molecules. Micelles only form when the concentration of the surfactant is greater than the critical micelle concentration (CMC). In some embodiments, the ophthalmic compositions of the present invention include and aqueous, clear mixed micellar solution.

In embodiments of the invention, surfactants are selected from the group consisting of polysorbate 80, polyoxyl 40 hydrogenated castor oil. The combination of polysorbate 80 and polyoxyl 40 hydrogenated castor oil and cyclosporine are used according to the present invention to enhance the bioavailability of cyclosporine in the pharmaceutical composition. Polysorbate 80 and polyoxyl 40 hydrogenated castor oil are the surfactants that solubilizes cyclosporine and incorporates cyclosporine into its micelles. The ophthalmic compositions according to the present invention comprise from about 0.05% to about 2% by weight of polysorbate 80, more preferably from about 0.5% to about 1% by weight, most preferably 0.9% by weight of polysorbate 80; and from about 0.3% to about 2% of polyoxyl 40 hydrogenated castor oil, more preferably from about 0.4% to about 1% by weight, most preferably 0.5% by weight of polyoxyl 40 hydrogenated castor oil.

In embodiments of the invention, cellulose polymers are selected from methylcellulose, hydroxy ethylcellulose, hydroxypropyl methylcellulose and sodiumcarboxy methyl cellulose. The preferred cellulose polymer used in the present invention is hydroxypropyl methylcellulose. In specific embodiments the ophthalmic composition of the present invention comprises from about 0.05% to about 5% by weight of hydroxypropyl methylcellulose, more preferably from about 0.1% to about 1% by weight and most preferably 0.5% by weight.

In embodiments of the invention, the solvents used in the present invention is selected from ethanol (USP) and water for Injection. In specific embodiments of the invention, ophthalmic compositions of the present invention comprise from about 0.1% to about 5% by weight of ethanol, more preferably from about 0.2% to about 1% by weight and most preferably 0.5% by weight. Water for Injection is further used as the additional solvent for the preparation of ophthalmic compositions of cyclosporine.

In embodiments of the present invention, tonicity adjusting agents used for the preparation of the ophthalmic composition include sodium chloride, potassium chloride, glycerol or mixtures thereof. In one embodiment, the solution contains 0.01% to 0.2% by weight of sodium chloride.

In embodiments of the invention, the ophthalmic compositions for the eye, are formulated at about pH 5 to about pH 8. The pH range may be achieved by addition of buffers to the composition. In an embodiment, the pH range in the composition in a formulation is about pH 6 to about pH 7.5. The compositions of the present disclosure may be buffered by any common buffer systems such as phosphate, borate, acetate, citrate, carbonate and borate-polyol complexes, with the pH and osmolality adjusted in accordance with well-known techniques to proper physiological values. The micellar compositions of the present disclosure are stable in the buffered aqueous solution.

In an embodiment, of a preservative is desired, the compositions may optionally be preserved with any of many well-known preservatives, including benzyl alcohol with/without EDTA, benzalkonium chloride, chlorhexidine. In certain embodiments, it may be desirable for a formulation as described herein to not include any preservatives. In this regard, preservatives may in some embodiments not be necessary or desirable in formulations included in single use containers. In other embodiments it may be advantageous to include preservatives, such as in certain embodiments in which the formulations are included in a multiuse container.

In embodiments of the present invention, the ophthalmic compositions optionally comprise pH adjusting agents selected from sodium hydroxide and/or hydrochloric acid.

In embodiments of the invention, the present invention provides the process for preparing the ophthalmic composition, said method comprising the steps of:
1. Dissolving the required amount of cyclosporine in ethanol to form a clear solution and
2. Addition of polysorbate 80 and polyoxyl 40 hydrogenated castor oil to above clear solution and required quantity of water for injection to form a homogenous solution
3. Aseptically filtrating the above homogenous solution
4. Adding required quantity of tamarind seed polysaccharide and hydroxypropyl methylcellulose to hot water for injection (prepared by heating required quantity of water for injection to 50° C. for 4 hours) and stirring to form a clear viscous solution.
5. Further adding the buffer system and sodium chloride as tonicity agent to the solution of step 4 and autoclaving the contents
6. Mixing the contents of step 3 and step 5
7. Adjusting the pH of the solution if required, and
8. filling the solution in unit dose vials.

In embodiments of the invention, ophthalmic compositions of the present invention are used for the treatment of ocular disorders which include Dry eye syndrome (DES, chronic dry eye, Keratitis sicca, Xerophthalmia; Keratoconjuctivitis sicca).

The present invention is also disclosed by the following non-limiting examples, according to some specific embodiments thereof, which illustrates examples of formulations based on cyclosporine, tamarind seed polysaccharide, hydroxypropylmethyl cellulose and polysorbate 80 which is used for the treatment of dry eye disease according to what is experimentally ascertained and reported in the experimental statement that follows.

EXAMPLES OF CYCLOSPORINE OPHTHALMIC COMPOSITIONS

Example 1

| Ingredients | % by weight |
| --- | --- |
| Cyclosporine | 0.05% to 2% |
| Tamarind seed polysaccharide | 0.05% to 5% |
| Hydroxypropyl methylcellulose | 0.05% to 5% |
| Polysorbate 80 | 0.05% to 2% |
| Sodium chloride | 0.01% to 0.2% |
| Ethanol | 0.1% to 5% |
| Sodium phosphate monobasic & sodium phosphate dibasic | q.s to pH 6 to pH 7.5 |
| Water for Injection | Q.s to 100% |

The product is prepared by the following steps:
1. Dissolving the cyclosporine in ethanol to form a clear solution and
2. Addition of polysorbate 80 to above clear solution and 50% of required quantity of water for injection to form a homogenous solution
3. Aseptically filtrating the above homogenous solution
4. Adding required quantity of tamarind seed polysaccharide and hydroxypropyl methylcellulose to hot water for injection (prepared by heating 50% of rest water for injection to 50° C. for 4 hours) and stirring to form a clear viscous solution.
5. Further adding the sodium phosphate monobasic & sodium phosphate dibasic and sodium chloride to the solution of step 4 and autoclaving the contents
6. Mixing the contents of step 3 and step 5
7. Adjusting the pH of the solution if required, and
8. filling the solution in unit dose vials.

Example 2

| Ingredients | % by weight |
| --- | --- |
| Cyclosporine | 0.05 |
| Tamarind seed polysaccharide | 0.2 |
| Hydroxypropyl methylcellulose | 1 |
| Polysorbate 80 | 0.9 |
| Sodium chloride | 0.65 |

| Ingredients | % by weight |
|---|---|
| Ethanol | 0.5 |
| Sodium phosphate monobasic & sodium phosphate dibasic | q.s |
| Water for Injection | Q.s to 100% |

The products are prepared are in same way as in example 1.

Example 3

| Ingredients | % by weight |
|---|---|
| Cyclosporine | 0.03% to 2% |
| Tamarind seed polysaccharide | 0.05% to 5% |
| Hydroxypropyl methylcellulose | 0.05% to 5% |
| Polysorbate 80 | 0.05% to 2% |
| polyoxyl 40 hydrogenated castor oil | 0.3% to 2% |
| Sodium chloride | 0.01% to 0.2% |
| Ethanol | 0.1% to 5% |
| Sodium phosphate monobasic & sodium phosphate dibasic | q.s to pH 6 to pH 7.5 |
| Water for Injection | Q.s to 100% |

The product is prepared by the following steps:
1. Dissolving the cyclosporine in ethanol to form a clear solution and
2. Addition of polysorbate 80 and polyoxyl 40 hydrogenated castor oil to above clear solution and 50% of required quantity of water for injection to form a homogenous solution
3. Aseptically filtrating the above homogenous solution
4. Adding required quantity of tamarind seed polysaccharide and hydroxypropyl methylcellulose to hot water for injection (prepared by heating 50% of rest water for injection to 50° C. for 4 hours) and stirring to form a clear viscous solution.
5. Further adding the sodium phosphate monobasic & sodium phosphate dibasic and sodium chloride to the solution of step 4 and autoclaving the contents
6. Mixing the contents of step 3 and step 5
7. Adjusting the pH of the solution if required, and
8. filling the solution in unit dose vials.

Examples 4 to 6

| Ingredients | Example 4 % by weight | Example 5 % by weight | Example 6 % by weight |
|---|---|---|---|
| Cyclosporine | 0.03 | 0.03 | 0.03 |
| Tamarind seed polysaccharide | 0.2 | 0.4 | 0.8 |
| Hydroxypropyl methylcellulose | 0.5 | 0.5 | 0.5 |
| Polysorbate 80 | 0.9 | 0.9 | 0.9 |
| polyoxyl 40 hydrogenated castor oil | 0.5 | 0.5 | 0.5 |
| Sodium chloride | 0.65 | 0.65 | 0.65 |
| Ethanol | 0.5 | 0.5 | 0.5 |
| Sodium phosphate monobasic & sodium phosphate dibasic | q.s | q.s | q.s |
| Water for Injection | q.s | q.s | q.s |

The products are prepared are in same way as in example 3.

Examples 7 to 9

| Ingredients | Example 7 % by weight | Example 8 % by weight | Example 9 % by weight |
|---|---|---|---|
| Cyclosporine | 0.05 | 0.05 | 0.05 |
| Tamarind seed polysaccharide | 0.2 | 0.4 | 0.8 |
| Hydroxypropyl methylcellulose | 0.5 | 0.5 | 0.5 |
| Polysorbate 80 | 0.9 | 0.9 | 0.9 |
| polyoxyl 40 hydrogenated castor oil | 0.5 | 0.5 | 0.5 |
| Sodium chloride | 0.65 | 0.65 | 0.65 |
| Ethanol | 0.5 | 0.5 | 0.5 |
| Sodium phosphate monobasic & sodium phosphate dibasic | q.s | q.s | q.s |
| Water for Injection | q.s | q.s | q.s |

The products are prepared are in same way as in example 3.

Examples 10 to 12

| Ingredients | Example 10 % by weight | Example 11 % by weight | Example 12 % by weight |
|---|---|---|---|
| Cyclosporine | 0.07 | 0.07 | 0.07 |
| Tamarind seed polysaccharide | 0.2 | 0.4 | 0.8 |
| Hydroxypropyl methylcellulose | 0.5 | 0.5 | 0.5 |
| Polysorbate 80 | 0.9 | 0.9 | 0.9 |
| polyoxyl 40 hydrogenated castor oil | 0.5 | 0.5 | 0.5 |
| Sodium chloride | 0.65 | 0.65 | 0.65 |
| Ethanol | 0.5 | 0.5 | 0.5 |
| Sodium phosphate monobasic & sodium phosphate dibasic | q.s | q.s | q.s |
| Water for Injection | q.s | q.s | q.s |

The products are prepared are in same way as in example 3.

COMPARATIVE EXAMPLES

Comparative Example 1 to 3

| Ingredients | Comparative Example 1 | Comparative Example 2 | Comparative Example 3 |
|---|---|---|---|
| Cyclosporine | — | 0.5 | — |
| Tamarind seed polysaccharide | 0.2 | — | — |

-continued

| Ingredients | Comparative Example 1 | Comparative Example 2 | Comparative Example 3 |
|---|---|---|---|
| Hydroxypropyl methylcellulose | 0.5 | 0.5 | 0.5 |
| Polysorbate 80 | 0.9 | 0.9 | 0.9 |
| polyoxyl 40 hydrogenated castor oil | 0.5 | 0.5 | 0.5 |
| Sodium chloride | 0.65 | 0.65 | 0.65 |
| Ethanol | 0.5 | 0.5 | 0.5 |
| Sodium phosphate monobasic & Sodium phosphate dibasic | q.s | q.s | q.s |
| Water for Injection | q.s | q.s | q.s |

The products are prepared are in same way as in example 3, removing the excipients wherever required.

Example 13: Cytotoxicity or Biocompatibility In-Vitro

Rabbit corneal epithelial cell line was sub cultured to (24 hours and 28 hour later) in T 25 and 75 cm² flask 2×10⁴ (20,000) cells per well to 96 well plate incubate in $CO_2$ incubator for overnight for 24 hours (90% of confluence). Discard the medium and load the formulations of Benzalkonium chloride (0.1%), Example-2 (8 nM & 10 µM), Restasis (8 nM & 10 µM) and Placebo (Example 2 without cyclosporine) with medium (5% of FBS) incubate for 4 hours and 24 hours. After 4 and 24 hours, add 10 µl of MTT solution (100 µl medium only and it should be yellow) up in medium to each well (Final conc. 0.5 mg/mL). Incubate for 30 minutes to 4 hours at 37° C., until intracellular purple formazan crystals are visible under microscope. Remove MTT and add solubilizing solution (DMSO) and incubate at room temperature or 37° C. for 30 minutes to 2 hours, until cells have lysed and purple crystals have dissolved. Remove plate cover and measure the absorbance at 570 nm in a micro plate reader. The results are tabulated in Table-1 (FIG. 1 & FIG. 2). Results indicate that Example 2 composition showed better compatibility in short term (4 hours) and long term (48 hours) when compared to Restasis (0.05% Cyclosporine Emulsion).

TABLE 1

| | % cell viability | |
|---|---|---|
| Compositions | 4 hours | 24 hours |
| Restasis 8 nM | 92 | 83 |
| Restasis 10 µM | 76 | 90 |
| Example 2 8 nM | 149 | 133 |
| Example 10 µM | 203 | 129 |

Example 14: In-Vitro Dry Eye Induction by Desiccation and Treatment

Rabbit corneal epithelial cells at a density of 2×10⁶ cells/well were seeded in 24 well plates, cultivated overnight and the medium was discarded by aspiration. The plates were left for 30 min with the cover left open in the clean bench to desiccate the cells. After 30 min each respective wells were added with different Example-2 compositions and Restasis (0.05% cyclosporine emulsion). Positive control was added with no media. Whereas negative control (culture media with cells) is not exposed to desiccation procedures. All the plates were incubated for 24 hours to assess the recovery of the cells after the treatment using MTT assay. Results are tabulated in Table-2 (FIG. 3). Results indicated after desiccation Example 2 compositions have more cell recovery, when compared to Restasis.

TABLE 2

| Composition | % cell recovery |
|---|---|
| Restasis 8 nM | 28 ± 2.3 |
| Restasis 10 µM | 22 ± 4.3 |
| Example 2 8 nM | 60 ± 3.8 |
| Example 10 µM | 37 ± 1.0 |

Example 15: In-Vitro Dry Eye Induction by UV Exposure and Treatment

Rabbit corneal epithelial cells at a density of 2×10⁶ cells/well were seeded in 24 well plates, cultivated overnight and the medium was discarded by aspiration. The plates were left open for 4 hours in biosafety cabinet with UV light on. Before irradiation, culture medium was removed, cells were rinsed once with phosphate-buffered saline (PBS 1×), covered with a thin PBS layer, and irradiated. To prevent the PBS overheating during irradiation, plates were kept on ice. negative control (culture media with 10% fetal bovine serum) and positive control (no culture media) were treated the same way as the Example-2 & Restasis compositions but were not exposed to UV rays. After 4 hours respective compositions were added and incubated for 24 hrs and cell viability was measured by MTT method. Results are represented Tabulated in Table-3 (FIG. 4). Results indicated after UV irradiation, Example 2 compositions have more cell recovery, when compared to Restasis.

TABLE 4

| Composition | % cell recovery |
|---|---|
| Restasis 8 nM | 61 ± 2.8 |
| Restasis 10 µM | 21 ± 1.43 |
| Example 2 8 nM | 81 ± 4.2 |
| Example 10 µM | 44 ± 1.5 |

Example 16: Invitro Corneal Regeneration

Rabbit corneal epithelial cells were seeded with a density of 3.2×10⁵ cells/well in 6 well plate incubated in $CO_2$ incubator for 24 h (90% of confluence). Corneal damage was induced by sterile pipette tip and washed with PBS followed by the addition of the test compounds. These cells were observed for migration and closure of the created wound. The wound closure distance was measured by Image J software. Wound distance is tabulated in Table-5 and images represented in FIG. 5.

TABLE 5

| Time (hr) | Control (mm) | Example -2 (mm) 10 µM | Restasis (mm) 10 µM |
|---|---|---|---|
| 0 | 0.697 | 0.697 | 0.697 |
| 24 | 0.287 | 0.471 | 0.676 |
| 48 | 0.123 | 0.330 | 0.657 |

Example 17: Invitro Permeation Studies

In vitro permeation studies were performed on a Franz diffusion cell with an effective diffusional area of 0.636 cm$^2$ and 4 mL of receiver chamber capacity using cellulose acetate membrane. The automated transdermal diffusion cell sampling system (Hansen diffusion systems) was used for these studies. Initially the donor compartment was empty and the receiver chamber was filled with artificial tear fluid. The receiver fluid was stirred with a magnetic rotor at a speed of 600 rpm, and the assembled apparatus was placed in the Hansen transdermal permeation apparatus and the temperature maintained at 32° C.±1° C. All the tear fluid was replaced every 30 minutes to stabilize the membrane. After complete stabilization 1 gm of formulations was placed into each donor compartment and sealed with paraffin film to provide occlusive conditions. Samples were withdrawn at regular intervals and analyzed for drug content by HPLC and results are tabulated in Table-6.

TABLE 6

| Time (hrs) | Restasis Avg. Release | Example-2 Avg. Release |
|---|---|---|
| 1 | 11.6 | 10.3 |
| 3 | 23.3 | 25.7 |
| 6 | 41.0 | 41.7 |
| 12 | 69.3 | 61.1 |
| 15 | 80.7 | 70.1 |
| 18 | 88.2 | 76.9 |
| 24 | 95.3 | 83.6 |

Example 18: Invitro Permeation Studies in Cell Monolayer

Rabbit corneal epithelial were seeded onto the filters at a concentration of 90,000 cells/cm$^2$. Cells added to the polyester and polycarbonate cell culture filters of costar (surface area, 4.7 cm$^2$; pore size, 0.4 and 3.0 mm; Transwell Clear, Transwell Costar. Cells were grown until they reach 90% confluency. Add the 2.6 ml of serum free medium basolateral side. Add 1.5 ml of Inhouse and Restasis samples with serum free medium in donor side. The cells grown at 37° C. in humidified air with 5% CO$_2$, for 4 hours samples of 500 µl were taken from receiver chamber and replaced by an equal volume of blank BSS buffer. Amount of cyclosporine was estimated by HPLC method and results are tabulated in Table-7.

TABLE 7

| Time (hrs) | Restasis (10 µM) Avg. Release | Example-2 (10 µM) Avg. Release |
|---|---|---|
| 4 | 24.06 | 38.76 |

Example 19: In Vivo Rabbit Dry Eye & Corneal Regeneration 2-2.5 kg body weight New Zealand (NZW) male rabbit were used in the study and the corneal injury was induced on Day 0 with filter paper soaked with 1N NaOH (kept on cornea for 60 seconds). After corneal damage the rabbits eye was washed with normal saline solution. In the same (each) animal dry eye was induced by Ophthalmic solution of atropine. All the rabbits were divided into 15 groups (n=8). The present inventive compositions of Examples 4, 5, 6, 7, 8, 9, 10, 11, 12, comparative example 1, 2 and 3, Restasis, normal control and negative control are installed into both the eyes of rabbits. Tear secretion measurement by Modified Schirmer's tear Test I and corneal injury observation under slit lamp method.

1. Modified Schirmer's Tear Test I: (STT1)

Each rabbit was manually restrained in a stand commercial rabbit restrainer and tested by using the modified STT1. End of a commercial tear-test paper was inserted over the lower lid margin at the juncture of the temporal and middle third of the lid. The length of tear strip wetted was recorded (in mm), which was indicated by the advancement of the blue dye on the marked standardized scale of the filter paper. STT1 was done for 5 minutes duration for each eye. Both eyes were tested at the same time. Test strips were held in place throughout the period of recording. All test strips were from the same lot and manufacturer (Tear Touch® Madhu Instrument Pvt Limited, New Delhi). The test is non-invasive and causes minimal distress to the rabbits. Tests were performed indoors in an environment of constant thermostatically controlled temperature and humidity. The same researcher tested all rabbits between 14:00 and 16:00. Hours. The results were depicted in FIGS. 6 and 7. All the compositions of inventive examples 4 to 12 have significant corneal regeneration ability when compared to Restasis. More preferably compositions with Examples 7, 8, 9 10, 11 and 12 showed significant corneal regeneration, and most preferably example 10, 11 and 12 showed more corneal regeneration.

2. Corneal Photographs (Slit Lamp Method):

The wound size was determined by staining the surface of the eye with commercially available Fluro Touch strips. Post staining of cornea. corneal photographs was taken with the help of digital camera attached to the slit lamp. Photographs were taken on following days 0, 1, 2, 3, 5, 7, 10, 14, 18 and 21 days. Epithelial wound healing Images will be taken at the slit lamp with a digital camera. Dimensions of the wound area will be measured using image analysis software (NIH Image J software) Wound closure will be expressed as a percentage of the initial wound area. The results were depicted in FIG. 8. All the compositions of inventive examples 4 to 12 have significant tear production ability when compared to Restasis.

Inventive composition of Example 7 to 12 showed significant improvement in both the corneal regeneration and tear fluid production.

We claim:

1. An ophthalmic composition consisting of
   (a) about 0.03% to about 2% by weight of cyclosporine,
   (b) about 0.05% to about 5% by weight of tamarind seed polysaccharide and
   (c) at least one pharmaceutically acceptable carrier selected from group consisting of surfactants, cellulose polymers, solvents, tonicity adjusting agents, buffers, pH adjusting agents and preservatives.

2. The ophthalmic composition according to claim 1, wherein said tamarind seed polysaccharide has a molecular weight comprised in the range of 450,000 Da to about 750,000 Da.

3. An ophthalmic composition consisting of
   (a) about 0.03% to about 2% by weight of cyclosporine,
   (b) about 0.05% to about 5% by weight of tamarind seed polysaccharide,
   (c) about 0.05% to about 5% by weight of hydroxypropyl methylcellulose,
   (d) about 0.05% to about 2% by weight of polysorbate 80, (e) about 0.3% to about 2% by weight of polyoxyl 40 hydrogenated castor oil,
(f) about 0.1% to about 5% by weight of ethanol,
(g) at least one pharmaceutically acceptable carrier selected from tonicity adjusting agent, buffer, pH adjusting agent, preservative and
(h) water.

4. The ophthalmic composition according to claim 3, wherein pH of the composition is of about 6.0 to about 7.5.

5. An ophthalmic composition consisting of
(a) about 0.07% by weight of cyclosporine,
(b) about 0.8% by weight of tamarind seed polysaccharide,
(c) about 0.9% by weight of polysorbate 80,
(d) about 0.5% by weight of polyoxyl 40 hydrogenated castor oil,
(e) about 0.5% by weight of hydroxypropyl methylcellulose,
(f) about 0.5% by weight of ethanol,
(g) at least one pharmaceutically acceptable carrier selected from tonicity adjusting agent, buffer, pH adjusting agent, preservative and
(h) water,
wherein pH of the composition is of about 6.0 to about 7.5.

* * * * *